(12) United States Patent
Gerke et al.

(10) Patent No.: US 10,235,708 B2
(45) Date of Patent: *Mar. 19, 2019

(54) PHOTOLABILE PRO-FRAGRANCES

(75) Inventors: Thomas Gerke, Duesseldorf (DE); Christian Kropf, Hilden (DE); Ursula Huchel, Cologne (DE); Axel Griesbeck, Cologne (DE); Olga Hinze, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 1549 days.

This patent is subject to a terminal disclaimer.

(21) Appl. No.: 13/586,113

(22) Filed: Aug. 15, 2012

(65) Prior Publication Data

US 2012/0308738 A1 Dec. 6, 2012

Related U.S. Application Data

(63) Continuation of application No. PCT/EP2011/050242, filed on Jan. 11, 2011.

(30) Foreign Application Priority Data

Feb. 17, 2010 (DE) .................. 10 2010 002 007

(51) Int. Cl.
*C07C 45/68* (2006.01)
*C07C 49/792* (2006.01)
*G06Q 30/06* (2012.01)

(52) U.S. Cl.
CPC .................. *G06Q 30/0635* (2013.01)

(58) Field of Classification Search
USPC .................. 568/327; 512/21; 424/70.1
See application file for complete search history.

(56) References Cited

U.S. PATENT DOCUMENTS

| 6,949,680 B2 | 9/2005 | Herrmann |
| 8,129,569 B2 | 3/2012 | Huchel et al. |
| 2008/0305063 A1 | 12/2008 | Huchel et al. |

FOREIGN PATENT DOCUMENTS

WO 01/96272 A2 12/2001

OTHER PUBLICATIONS

Neckers, Douglas C. Developmental Photochemistry. The Norrish Type II Reaction. Journal of Organic Chemistry, 1971, vol. 36 (13), 1838-1840.*
Croft et al. The Chemistry of Eremophila spp. XXI Structural Study of a New Eremane Diterpene. Australian Journal of Chemistry, 1984, vol. 37, 785-793.*
PCT International Search Report (PCT/EP2011/050242) dated Jul. 26, 2011.
Marek Majewski et al, "Reactions of .beta.pinene with Aromatic Aldehydes", Synthetic Communications, vol. 20, No. 16, pp. 2549-2558, 1990.
Xiao Zhuanquan et al, "Synthesis of Endo-.alpha.-isocamphanyl Ketones and .beta.-isocamphanyl Alcohols", Chemistry and Industry of Forest Products / Lin Chan Hua Xue Yu Gong Ye, Chinese Electronic Periodical Services, vol. 16, No. 3, pp. 19-23, 1996.
Herbert Charles Brown et al, "Reaction of B-Alkyl-9-borabicyclo[3.3.1]nonanes with .alpha.-Bromo Ketones Under the Influence of Potassium Tert-Butoxide. A Convenient Procedure for the .alpha. Alkylation of Ketones", Journal of the American Chemical Society, vol. 91, No. 8, pp. 2147-2149, 1969.
C. Wade Downey et al, "One-Pot Enol Silane Formation-Mukaiyama Aldol-Type Addition to Dimethyl Acetal Mediated by TMSOTf", The Journal of Organic Chemistry, vol. 73, No. 8, pp. 3299-3302, 2008.
Guangrong Zheng et al, "Lobelane Analogues as Novel Ligands for the Vesicular Monoamine Transporter-2", Bioorganic & Medicinal Chemistry, vol. 13, No. 12, pp. 3899-3909, 2005.
C. Kishan Reddy et al, "New Cobalt- and Iron-Catalyzed Reactions of Organozinc Compounds", Angewandte Chemie (International Edition in English), vol. 108, No. 15, pp. 1700-1701, 1996.
P. Zhong et al, "New Synthetic Route to Ketones from Camphene and .beta.-pinene", Chemistry of Natural Compounds, vol. 39, No. 6, pp. 549-552, 2003.
Donald D. Phillips et al, "The Friedel-Crafts Condensation of trans-2-Hydroxycyclohexaneacetic Acid Lactone with Aromatic Hydrocarbons. I. Benzene and Naphthalene", Journal of the American Chemical Society, vol. 80, No. 6, pp. 1360-1366, 1958.
Rosa Ortiz et al, "Tandem Intramolecular Carbolithiation-transmetallation: from Lithium to Copper or Boron Chemistry", Tetrahedron, vol. 61, No. 7, pp. 1699-1707, 2005.
Chrysa F. Malosh et al, "Catalytic Cross-Coupling of Alkylzinc Halides with .alpha.-Chloroketones", Journal of the American Chemical Society, vol. 126, No. 33, pp. 10240-10241, 2004.
Viktor V. Zhdankin et al, "Carbon-Carbon Bond Formation in Reactions of PhIO.HBF4/Silyl Enol Ether Adduct with Alkenes or Silyl Enol Ethers", The Journal of Organic Chemistry, vol. 54, No. 11, pp. 2605-2608, 1989.
Roger L. Snowden et al, "Fragmentation of Homoallylic Alkoxides. Thermolysis of Potassium 2-Substituted Bicyclo [2.2.2]oct-5-en-2-alkoxides", Helvetica Chimica Acta, vol. 64, No. 7, pp. 2913-2202, 1981.
Andrei V. Malkov et al, "Molybdenum(II)- and Tungsten(II)-Catalyzed Allylic Substitution", Journal of Organic Chemistry, vol. 64, No. 8, pp. 2737-2750, 1999.
Nobuharu Iwasawa et al, "Synthesis of Medium-Sized Bicyclic Compounds by Intramolecular Cyclization of Cyclic .beta.-Keto Radicals Generated from Cyclopropanols Using Manganese(III) Tris(pyridine-2-carboxylate) and its Application to Total Synthesis of 10-Isothiocyanatoguaia-6-ene", Bulletin of the Chemical Society of Japan, vol. 72, No. 1, pp. 85-97, 1999.

(Continued)

*Primary Examiner* — Sikarl Witherspoon
(74) *Attorney, Agent, or Firm* — David K. Benson

(57) ABSTRACT

Photolabile scent storage substance that are capable of photoinduced release of cyclic compounds have at least one cyclic double bond. These scent storage substances are special ketones, and enable greatly improved stability of the scent impression, in particular with a fresh character, in typical applications, for example in textile laundering, room scenting, and in the cosmetic sector. More economical utilization of the stored scents can thereby be ensured. Also described are corresponding washing or cleaning agents, scenting methods, and methods for manufacturing the special ketones.

10 Claims, No Drawings

(56) References Cited

OTHER PUBLICATIONS

An Pai Li et al, "First Total Synthesis of an Analogue of (+−)-Hypargenin B", Chinese Chemical Letters, vol. 13, No. 2, pp. 133-134, 2002.
Jerry March, "Advanced Organic Chemistry—Reactions, Mechanisms, and Structure, Fourth Edition", pp. 783-789, 1992.

* cited by examiner

PHOTOLABILE PRO-FRAGRANCES

CROSS-REFERENCES TO RELATED APPLICATIONS

This application is a continuation of PCT/EP2011/050242, filed on Jan. 11, 2011, which claims priority under 35 U.S.C. § 119 to DE 10 2010 002 007.9 filed on Feb. 17, 2010, both of which are hereby incorporated by reference.

FIELD OF THE INVENTION

The present invention generally relates to scent storage substances, such as those used, for example, in washing or cleaning agents or in cosmetics, and more particularly relates to special ketones that function as photolabile scent storage substances. The present invention further relates to washing or cleaning agents, cosmetic agents, and air freshening agents that contain such ketones. It further relates to a method for long-lasting scenting of surfaces, and also to a method for long-lasting room scenting. It further relates to a method for manufacturing the aforesaid ketone.

BACKGROUND OF THE INVENTION

Washing and cleaning agents and/or cosmetic agents usually contain scents that impart a pleasant and fresh odor to the agents. The scents usually mask the inherent scent note of the other ingredients, producing a positive odor impression in the consumer. In the sector of washing agents, scents are particularly important constituents of the composition, since the laundry should have a pleasant and fresh smell both when wet and when dry. A fundamental problem in the utilization of scents consists in the fact that these substances are volatile substances, since otherwise a scent effect could not be achieved. The problem faced when using scents, for example, in washing and cleaning agents, and also for use in cosmetic agents, is thus that despite the volatility of the compounds, it is desirable to produce a long-lasting scent effect that is as consistent as possible. In addition, the scent impression of a perfume changes over time, since the fragrances that represent the fresh and light notes of the perfume volatilize more quickly, because of their high vapor pressure, than the scents which represent the middle and base notes.

One approach to solving this problem involves applying scents onto carrier materials and coating the scented carriers, or encapsulating scents or incorporating them into compounds (for example, cyclodextrin-perfume complexes). A further possibility that exists is to bond the scents chemically to carrier media, the chemical bond being slowly broken and the scent released as a result. This kind of carrier-bound precursor form of a scent is also known as a "pro-fragrance" or scent storage substance. In this connection, International Patent Application WO 2007/087977 discloses the use of 1-aza-3,7-dioxabicyclo[3.3.0]octane compounds as scent storage substances for delayed release of scent aldehydes and scent ketones by hydrolysis. An alternative possibility for delayed release of scents is represented by the use of so-called photoactivatable substances as scent storage substances. The action of sunlight or another electromagnetic radiation source of a specific wavelength induces breakage of a covalent bond in the scent storage substance molecule, thereby releasing a scent. For effective release of the scent, the above-described process must tolerate the presence of oxygen and water.

In this connection, U.S. Pat. No. 6,949,680 discloses the use of specific phenyl ketones or pyridyl ketones as photoactivatable substances that, in a photochemical fragmentation, release a terminal alkene as an active substance in the presence of light. The aforesaid active substance possesses, for example, a scent-imparting or antimicrobial activity that is first delayed by the photochemically induced decomposition, and over a longer period of time is released on a specific surface. The aforesaid photolabile phenyl ketones or pyridyl ketones constituting scent storage substances are manufactured in a complex, multi-step synthesis method using protecting-group operations; the synthesis must be individually adapted for each individual active substance. WO 2009/118219 A1 describes, as scent storage substances, photoactivatable substances that permit delayed release of cyclic alkenes having a so-called semicyclic double bond.

Accordingly, it is desirable to make available photoactivatable substances, constituting scent storage substances, that permit the delayed release of cyclic compounds having at least one cyclic double bond, in particular of cyclic terpenes or cyclic terpenoids having at least one cyclic double bond. In addition, it is desirable to make available a simple and economical synthesis method for manufacturing the aforesaid scent storage substances.

In view of this, desirable features and characteristics of the present invention will become apparent from the subsequent detailed description of the invention and the appended claims, taken in conjunction with the accompanying drawings and this background of the invention.

BRIEF SUMMARY OF THE INVENTION

A ketone of the general formula (I)

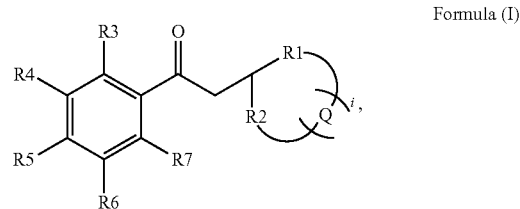

Formula (I)

where i=1 or 2; R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms; and R1 and R2, mutually independently, denote a secondary, tertiary, or quaternary carbon atom; and Q denotes at least one divalent substituted or unsubstituted group bridging R1 and R2 and having 1 to 10 carbon atoms.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found, surprisingly, that certain cyclic phenyl ketones, constituting photoactivatable scent storage substances, permit the delayed release of cyclic compounds having at least one cyclic double bond. The subject matter of the present invention is therefore a ketone of the general formula (I)

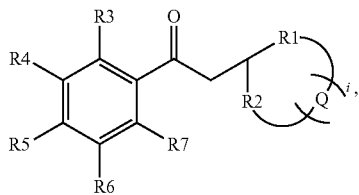

Formula (I)

where i=1 or 2,
R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms, and
R1 and R2, mutually independently, denote a secondary, tertiary, or quaternary carbon atom, and
Q denotes at least one divalent substituted or unsubstituted group bridging R1 and R2 and having 1 to 10 carbon atoms.

The term "secondary carbon atom" is to be understood for purposes of the invention as a carbon atom that is covalently bonded to two further carbon atoms. The terms "tertiary carbon atom" and "quaternary carbon atom" are to be understood for purposes of the invention as, respectively, a carbon atom that is covalently bonded to three or four further carbon atoms.

The scent storage substances according to the present invention permit the delayed release of cyclic compounds having at least one cyclic double bond, which refers, for example, to the olfactorily significant class of the cyclic terpenes having a cyclic double bond. These represent an important class of fragrances. They can, for example, contribute to imparting a pleasant and fresh odor to washing or cleaning agents or to cosmetic agents. They are notable as a rule for their high vapor pressure, and because of their low degree of functionalization are difficult to bind chemically to conventional carrier media. The scent storage substances according to the present invention allow the aforesaid cyclic compounds to be released over a longer period of time. Use of the scent storage substances according to the present invention in washing, cleaning, or care-providing agents resulted, in the context of their utilization, in an improved long-term scent effect, in particular in conjunction with textile treatment. For example, with the use of scent storage substances according to the present invention in a laundry treatment agent, for example a washing agent and a fabric softener, it was possible to observe an improved long-term scent effect in the treated laundry. In addition, corresponding products have particularly good shelf stability. The agents according to the present invention further make it possible to reduce the total quantity of perfume contained in the agent, but nevertheless to achieve odor advantages on the washed textiles, in particular with regard to perceived freshness. The slow release of the stored fragrance occurs after the action of light encompassing the wavelengths from 200 to 400 nm.

In a particularly preferred embodiment of the invention, R1 and R2, mutually independently, denote a secondary or tertiary carbon atom. In a very particularly preferred embodiment of the invention, one of the two residues R1 and R2 denotes a secondary carbon atom, while the respective other residue denotes a tertiary carbon atom.

A further subject of the present invention is a washing or cleaning agent (such as, by preference, a textile or surface treatment agent, textile washing agent, fabric softener) containing at least one ketone of the general formula (I) as defined above, said ketone being contained by preference in quantities between 0.0001 and 5 wt %, advantageously between 0.001 and 4 wt %, more advantageously between 0.01 and 3 wt %, in particular between 0.5 and 2 wt %, based in each case on the total agent.

Suitable cleaning agents are, for example cleaning agents for hard surfaces, such as by preference dishwashing agents. The cleaning agents can also, for example, be household cleaners, all-purpose cleaners, window cleaners, floor cleaners, etc. The product can by preference be one for cleaning toilet bowls and urinals, advantageously a toilet flush cleaner for suspension in the toilet bowl, in particular a so-called toilet block.

A further subject of the present invention is a cosmetic agent containing at least one ketone of the general formula (I) as defined above, said ketone being contained by preference in quantities between 0.0001 and 5 wt %, advantageously between 0.001 and 4 wt %, more advantageously between 0.01 and 3 wt %, in particular between 0.5 and 2 wt %, based in each case on the total agent.

A further subject of the present invention is an air freshening agent (e.g. room air freshener, room deodorant, room spray, etc.) containing at least one ketone of the general formula (I) as defined above, said ketone being contained by preference in quantities between 0.0001 and 5 wt %, advantageously between 0.01 and 5 wt %, more advantageously between 0.1 and 3 wt %, in particular between 0.5 and 2 wt %, based in each case on the total agent.

A further subject of the present invention is a method for long-lasting scenting of surfaces (such as, for example, textiles or hard surfaces, skin, hair), where a ketone according to the present invention of the general formula (I), or an agent according to the present invention (such as, for example, a washing or cleaning agent, a cosmetic agent) containing a ketone according to the present invention, is applied onto the surface to be scented (such as, for example, a textile, hard surface, skin, hair), and said surface is then exposed to an electromagnetic radiation encompassing the wavelengths from 200 to 400 nm. Natural sunlight can by preference be regarded as an "electromagnetic radiation" for purposes of the present invention.

A further subject of the invention is a method for long-lasting room scenting, an air freshening agent according to the present invention being exposed to an electromagnetic radiation encompassing the wavelengths from 200 to 400 nm.

Also a subject of the present invention is a method for manufacturing a ketone according to the present invention of the general formula (I), encompassing the following steps:
a) hydroboration of a compound of the general formula (III)

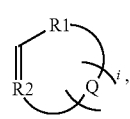

Formula (III)

where i=1 or 2, and R1 and R2, mutually independently, denote a secondary, tertiary, or quaternary carbon atom and Q denotes at least one divalent substituted or unsubstituted group bridging R1 and R2 and having 1 to 10 carbon atoms, b) reacting the organoborane adduct produced in step a) with a compound of the general formula (IV)

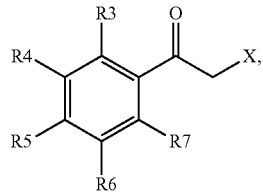

Formula (IV)

where X is a halogen atom and R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms.

Another subject of the invention is the use of a ketone according to the present invention of the general formula (I) as a scent storage substance, and the use of a ketone according to the present invention in washing or cleaning agents (such as, in particular, liquid or solid washing agents, fabric softeners, softening washing agents, washing adjuvants) or in cosmetic agents or in air freshening agents.

Likewise a subject of the present invention is the use of the ketones according to the present invention, in particular contained in agents according to the present invention such as, for example, washing or cleaning agents or cosmetic agents, to improve scent efficiency, in particular on textiles, for example in the context of automatic textile laundering.

A ketone according the present invention of the general formula (I) in which i 2, and at least one of the divalent substituted or unsubstituted groups Q bridging R1 and R2 encompasses 2 to 6 carbon atoms, is preferred for purposes of the invention.

A ketone according to the present invention of the general formula (I) in which i=2, and one of the divalent groups Q bridging R1 and R2 is unbranched and encompasses 2, 3, or 4 carbon atoms, in particular 3 or 4 carbon atoms, is particularly preferred.

Likewise preferred is a ketone according to the present invention of the general formula (I) in which i=2 and one of the divalent groups Q bridging R1 and R2 is branched, and the shortest direct connection between R1 and R2 is constituted from 2, 3, or 4 carbon atoms respectively covalently linked to one another. Very particularly preferred for purposes of the invention is a ketone according to the present invention of the general formula (I) in which i=2 and one of the divalent groups Q bridging R1 and R2 is unbranched and encompasses 2, 3, or 4 carbon atoms, in particular 3 or 4 carbon atoms, while the other divalent group Q bridging R1 and R2 is branched, and the shortest direct connection between R1 and R2 is constituted from 2, 3, or 4 carbon atoms respectively covalently linked to one another.

Likewise preferred for purposes of the invention is a ketone according to the present invention of the general formula (I) in which R1 and/or R2 and/or at least one divalent group Q bridging R1 and R2 has a substitution with at least one heteroatom selected from the group constituted from N, O, or S. A ketone according to the present invention of the general formula (I) in which R1 and/or R2 and/or at least one divalent group Q bridging R1 and R2 has a substitution in the form of an —OH, —$OR^a$, —SH, —$SR^b$, or —$NR^cR^d$ group, where $R^a$, $R^b$, $R^c$, and $R^d$ are selected, mutually independently, from the group consisting of hydrogen and branched or unbranched, substituted or unsubstituted alkyl groups that encompass 1 to 10, in particular 1 to 4, and particularly preferably 1, 2, or 3 carbon atoms, is particularly preferred.

Likewise particularly preferred is a ketone according to the present invention of the general formula (I) in which a divalent group Q bridging R1 and R2 encompasses a ketone structure, carboxylic-acid structure, lactone structure, amide structure, ester structure, and/or aldehyde structure.

Also preferred is a ketone according to the present invention of the general formula (I) in which four of the five aryl substituents R3, R4, R5, R6, and R7 denote hydrogen. R3, R4, R6, and R7 by preference denote hydrogen, while the substituent in the R5 para-position denotes a halogen atom, in particular —F, —Cl, or —Br, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 denotes —Cl, —Br, —$NO_2$, or an alkyl or alkoxy group encompassing 1 to 4 carbon atoms. By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group.

A substitution in the para-position (R5) is particularly preferred because the electron structure of the aromatic ring can be most effectively modified here, with the result that the absorption maximum of ketones of the general formula (I) can easily be adapted to a specific wavelength.

Likewise preferred is a ketone according to the present invention of the general formula (I) in which R3, R4, R5, R6, and R7 denote hydrogen.

Further preferred for purposes of the invention is a ketone according to the present invention of the general formula (I) from which, by cleavage of a carbon bond, a ketone of the general formula (II)

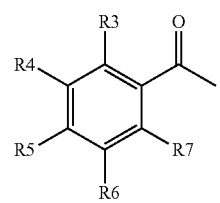

Formula (II)

and a compound of the general formula (III)

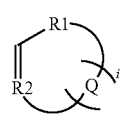

Formula (III)

are formed, where i=1 or 2, R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms, and R1 and R2, mutually independently, denote a secondary, tertiary, or quaternary carbon atom, and Q denotes at least one divalent substituted or unsubstituted group bridging R1 and R2 and having 1 to 10 carbon atoms.

In a particularly preferred embodiment of the invention, R1 and R2 in formula (III) denote, mutually independently, a secondary or tertiary carbon atom. In a very particularly preferred embodiment of the invention, one of the two residues R1 and R2 denotes a secondary carbon atom, while the respective other residue denotes a tertiary carbon atom.

A compound according to the present invention of the general formula (II) in which four of the five aryl substituents R3, R4, R5, R6, and R7 denote hydrogen, is preferred. By preference, R3, R4, R6, and R7 denote hydrogen, while the substituent in the R5 para-position denotes a halogen atom, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 denotes —Cl, —Br, —$NO_2$, or an alkyl or alkoxy group encompassing 1 to 4 carbon atoms.

By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group.

A ketone according to the present invention of the general formula (I) from which proceeds, by cleavage of a carbon bond, a compound of the general formula (III) in which i=2 and at least one of the divalent substituted or unsubstituted groups Q bridging R1 and R2 encompasses 2 to 6 carbon atoms, is preferred for purposes of the invention.

Particularly preferred in this context is a compound of the general formula (III) in which i=2 and one of the divalent groups Q bridging R1 and R2 is unbranched and encompasses 2, 3, or 4 carbon atoms, in particular 3 or 4 carbon atoms.

Likewise preferred is a compound of the general formula (III) in which i=2 and one of the divalent groups Q bridging R1 and R2 is branched, and the shortest direct connection between R1 and R2 is constituted from 2, 3, or 4 carbon atoms respectively covalently linked to one another.

Very particularly preferred for purposes of the invention is a ketone according to the present invention of the general formula (I) from which proceeds, by cleavage of a carbon bond, a compound of the general formula (III) in which i=2 and one of the divalent groups Q bridging R1 and R2 is unbranched and encompasses 2, 3, or 4 carbon atoms, in particular 3 or 4 carbon atoms, while the other divalent group Q bridging R1 and R2 is branched, and the shortest direct connection between R1 and R2 is constituted from 2, 3, or 4 carbon atoms respectively covalently linked to one another.

Likewise preferred for purposes of the invention is a compound of the general formula (III) in which R1 and/or R2 and/or at least one divalent group Q bridging R1 and R2 has a substitution with at least one heteroatom selected from the group consisting of N, O, or S. A compound of the general formula (III) in which R1 and/or R2 and/or at least one divalent group Q bridging R1 and R2 has a substitution in the form of an —OH, —$OR^a$, —SH, —$SR^b$, or —$NR^cR^d$ group, where $R^a$, $R^b$, $R^c$, and $R^d$ are selected, mutually independently, from the group consisting of hydrogen and branched or unbranched, substituted or unsubstituted alkyl groups that encompass 1 to 10 carbon atoms, is particularly preferred.

Likewise particularly preferred is a compound of the general formula (III) in which a divalent group Q bridging R1 and R2 encompasses a ketone structure, carboxylic-acid structure, lactone structure, amide structure, ester structure, and/or aldehyde structure.

Also preferred is a compound of the general formula (III) which is a cyclic terpene or cyclic terpenoid having at least one cyclic double bond.

"Terpenes" are to be understood according to the present invention as natural substances constructed from isoprene basic units, and derivatives.

"Terpenoids" are to be understood according to the present invention as natural substances constructed from isoprene basic units, and derivatives, that have a high degree of structural affinity with the terpenes but differ from them, for example, by the loss or rearrangement of a fragment, preferably of a methyl group.

Depending on the number of basic units, the terpene units are classified as monoterpenes, sesquiterpenes, diterpenes, sesterpenes, triterpenes, and tetraterpenes.

According to a preferred embodiment, monocyclic monoterpenes, bicyclic monoterpenes, and cyclic sesquiterpenes are preferred. All terpenes according to the present invention encompass at least one cyclic double bond.

Particularly preferred cyclic terpenes or cyclic terpenoids having a cyclic double bond are selected from the group consisting of α-pinene, α-terpinene, limonene, β-bisabolene, humulene, terpinolene, phellandrene, trichodiene, and from enantiomers and/or diastereomers thereof.

The aforesaid cyclic terpenes or cyclic terpenoids are as a rule notable for a high tendency toward isomerization. Long exposure to sunlight can result in skeleton rearrangements (e.g. as a result of Wagner-Meerwein rearrangements) or in the formation of double-bond isomers. This is undesirable, since the aforesaid isomers often differ considerably, in terms of their odor impression, from the cyclic terpenes or cyclic terpenoids that were originally present. In some circumstances, the scent impression of a multi-component perfume oil mixture can be decisively modified as a result. An advantage of the present invention is therefore the fact that the terpenes or terpenoids according to the present invention are released only directly upon utilization, as a result of sunlight exposure, with the result that a change in scent due to previous isomerization reactions can be almost ruled out.

A subject of the present invention is likewise an agent (such as, in particular, a washing or cleaning agent, cosmetic agent, or air freshening agent) containing at least one compound of the general formula (Ia)

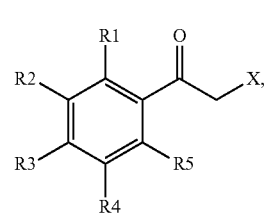

Formula (Ia)

where R1, R2, R3, R4, and R5, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms, and X denotes, after cleavage of the C—X bond, a cyclic compound containing at least one cyclic double bond.

In a particularly preferred embodiment, the residue X after cleavage of the C—X bond is a cyclic terpene having a cyclic double bond, selected by preference from α-pinene, α-terpinene, limonene, β-bisabolene, humulene, terpinolene, phellandrene, trichodiene, and from enantiomers and/or diastereomers thereof.

A compound according to the present invention of the general formula (Ia) in which four of the five aryl substituents R3, R4, R5, R6, and R7 denote hydrogen is preferred. R3, R4, R6, and R7 by preference denote hydrogen, while the substituent in the R5 para-position denotes a halogen atom, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 denotes —Cl, —Br, —$NO_2$, or an alkyl or alkoxy group encompassing 1 to 4 carbon atoms. By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group.

In a preferred embodiment of the invention, an agent according to the present invention, e.g. a washing or cleaning agent or cosmetic agent, contains at least one further scent. The scents and/or perfume oils preferably used are subject to no limitations at all. For example, synthetic or natural fragrance compounds of the ester, ether, aldehyde (scent aldehyde), ketone (scent ketone), alcohol, hydrocarbon, acid, carbonic acid ester, aromatic hydrocarbon, aliphatic hydrocarbon, saturated and/or unsaturated hydrocarbon types, and mixtures thereof, can be used by preference as scents.

All usual scent aldehydes and scent ketones that are typically used to bring about a pleasant scent sensation can be used in this context as scent aldehydes or scent ketones. Suitable scent aldehydes and scent ketones are commonly known to the skilled artisan. The scent ketones can encompass all ketones that can impart a desired scent or a fresh sensation. Mixtures of different ketones can also be used. Usable ketones are, for example, alpha-damascone, delta-damascone, isodamascone, carvone, gamma-methyl ionone, Iso-E-Super, 2,4,4,7-tetramethyl-oct-6-en-3-one, benzylacetone, beta-damascone, damascenone, methyldihydrojasmonate, methyl cedrylone, hedione, and mixtures thereof. Suitable scent aldehydes can be any aldehydes that, correspondingly to the scent ketones, convey a desired scent or a fresh sensation. These can once again be individual aldehydes or aldehyde mixtures. Suitable aldehydes are, for example, melonal, triplal, ligustral, adoxal, lilial, etc. The scent aldehydes and scent ketones have an aliphatic, cycloaliphatic, aromatic, ethylenically unsaturated structure, or a combination of said structures. In addition, further heteroatoms or polycyclic structures can be present. The structures can comprise suitable substituents, such as hydroxyl or amino groups. For further suitable scents selected from aldehydes and ketones, reference is made to the work of Steffen Aretander published 1960 and 1969 respectively, reprinted 2000; ISBN: Aroma Chemicals Vol. 1: 0-931710-37-5, Aroma Chemicals Vol. 2: 0-931710-38-3. Suitable scents of the ester type are, for example benzyl acetate, phenoxyethylisobutyrate, p-tert-butylcyclohexyl acetate, etc. Fragrance compounds of the hydrocarbon type are, for example, terpenes such as limonene and pinene. Suitable scents of the ether type are, for example, benzyl ethyl ether and ambroxan. Suitable scent alcohols are, for example 10-undecen-1-ol, 2,6-dimethylheptan-2-ol, 2-methylbutanol, 2-methylpentanol, 2-phenoxyethanol, 2-phenylpropanol, etc. Scents and/or perfume oils can also be natural fragrance mixtures such as those accessible from plant sources. The scents and/or perfume oils can also be essential oils such as, for example, angelica oil, anise oil, arnica flower oil, etc. The total quantity of the at least one scent in the agent according to the present invention such as, for example, a washing or cleaning agent or cosmetic agent is by preference between 0.001 and 5 wt %, advantageously between 0.01 and 4 wt %, with further advantage between 0.1 and 3 wt %, and very particularly preferably between 0.5 and 2 wt %, based on the total agent. It is preferred to use mixtures of different scents (from the different aforementioned scent classes) that together produce an attractive scent note.

In a further preferred embodiment of the invention, agents according to the present invention (such as, for example, washing or cleaning agents or cosmetic agents) contain at least one surfactant, selected by preference from the group consisting of anionic, cationic, nonionic, zwitterionic, amphoteric surfactants, or mixtures thereof.

An agent according to the present invention can by preference be solid or liquid; liquid agents, in particular washing agents, are preferred. Especially for the case in which the agent according to the present invention is a washing agent, it is preferred that it contain at least one surfactant selected from the group made up of anionic, nonionic, zwitterionic, and amphoteric surfactants. Especially for the case in which the agent according to the present invention is a softening washing agent ("2 in 1"), it is preferred that it contain a softening component as well as at least one surfactant selected from the group consisting of anionic, nonionic, zwitterionic, and amphoteric surfactants. Washing adjuvants are used for targeted pretreatment of the laundry before washing, in a context of spots or heavy staining. The washing adjuvants include, for example, pretreatment agents, soaking agents, decolorants, and spot remover.

Especially for the case in which the agent according to the present invention is a fabric softener, it is preferred that it contain a softening component. Fabric softeners are preferred as agents according to the present invention because they come into contact with the textiles only in the last step of a conventional textile washing operation (the rinse cycle), and a quantity of scents that is large as possible can thus absorb onto the textile with no risk that the scents will be removed again in subsequent steps. It is very particularly preferred that the softening component be an alkylated quaternary ammonium compound, at least one alkyl chain being interrupted by an ester group or amido group. The softening component encompasses, for example, quaternary ammonium compounds such as monoalk(en)yltrimethylammonium compounds, dialk(en)yldimethylammonium compounds, mono-, di- or triesters of fatty acids with alkanolamines. Further softening components usable according to the present invention are represented by quaternized protein hydrolysates or protonated amines Cationic polymers are also suitable softening components. Also usable are polyquaternized polymers (e.g. Luviquat® Care of BASF) and also chitin-based cationic biopolymers and derivatives thereof, for example the polymer obtainable under the commercial designation Chitosan® (manufacturer: Cognis). Further suitable softening components encompass protonated or quaternized polyamines. Particularly preferred softening components are alkylated quaternary ammonium compounds of which at least one alkyl chain is interrupted by an ester group and/or amido group. N-Methyl-N-(2-hydroxyethyl)-N,N-(ditallowacyloxyethyl)ammonium methosulfate or bis-(palmitoyloxyethyl)hydroxyethylmethylammonium methosulfate are very particularly preferred.

The agent according to the present invention, especially in the form of fabric softeners, can also contain nonionic softening components such as, chiefly, polyoxyalkylene glycerol alkanoates, polybutylenes, long-chain fatty acids, ethoxylated fatty acid ethanolamides, alkyl polyglucosides, in particular sorbitan mono-, di-, and triesters, and fatty acid esters of polycarboxylic acids. In the fabric softener according to the present invention constituting an agent according to the present invention, the softening component is contained advantageously in quantities from 0.1 to 80 wt %, usually 1 to 40 wt %, by preference 2 to 20 wt %, and in particular 3 to 15 wt %, and the at least one scent or the mixture of different scents is contained in quantities advantageously from 0.1 to 20 wt %, by preference 1 to 13 wt %, and in particular 2 to 8 wt %, based in each case on the total quantity of the agent according to the present invention.

The agent according to the present invention, in particular in the form of a fabric softener, can optionally contain as a further component one or more nonionic surfactants; those that are usually also utilized in washing agents can be used.

It is further preferred that the agent according to the present invention, especially in the form of a washing or cleaning agent, additionally contain further advantageous ingredients that are known to the skilled artisan. The agent according to the present invention, such as in particular a washing or cleaning agent, can thus contain, in addition to the surfactants and/or softening compounds, further ingredients that further improve the applications-engineering and/or aesthetic properties of the agent. In the context of the present invention, preferred agents additionally contain one or more substances from the group of the detergency builders, bleaching agents, bleach activators, enzymes, electrolytes, nonaqueous solvents, pH adjusting agents, perfumes, perfume carriers, fluorescing agents, dyes, hydrotopes, foam inhibitors, silicone oils, antiredeposition agents, optical brighteners, anti-gray agents, shrinkage preventers, wrinkle-prevention agents, color transfer inhibitors, antimicrobial active substances, germicides, fungicides, antioxidants, preservatives, corrosion inhibitors, antistatic agents, bittering agents, ironing adjuvants, proofing and impregnation agents, swelling and anti-slip agents, neutral filler salts, and UV absorbers. Silicates, aluminum silicates (in particular zeolites), carbonates, salts of organic di- and polycarboxylic acids, and mixtures of said substances may be recited, in particular, as detergency builders that can be contained in the agents according to the present invention.

As a cleaning agent, the agent according to the present invention can be used, for example, to clean hard surfaces. This can refer, for example, to dishwashing agents that are used for manual or automatic cleaning of tableware. It can also refer to usual industrial or household cleaners with which hard surfaces such as furniture surfaces, floor tiles, wall tiles, and wall and floor coverings are cleaned. Possible hard surfaces are not only tableware but also all other hard surfaces, in particular made of glass, ceramic, plastic, or metal, in the home and commercially. As with all other agents according to the present invention, the formulations can be solid or liquid; solid formulations can exist as a powder, granulate, extrudate, in tab form, as a tablet, or as a pressed and/or melted shaped element. Liquid formulations can be solutions, emulsions, dispersions, suspensions, microemulsions, gels, or pastes.

The manufacture of solid agents according to the present invention (i.e. washing or cleaning agents) presents no difficulties and can in principle occur in known fashion, for example by spray-drying or granulation; an optional peroxygen compound and optional bleach catalyst can, if applicable, be added later. A method comprising an extrusion step is preferred for the manufacture of agents according to the present invention having an elevated bulk weight, in particular in the range from 650 g/l to 950 g/l. The manufacture of liquid agents according to the present invention likewise presents no difficulties and can likewise occur in known fashion. The scent storage substances according to the present invention can, in particular, be incorporated together with other fragrances.

The method for manufacturing a ketone according to the present invention of the general formula (I) has already been recited above as a further subject of the invention, said method encompassing hydroboration as step a), and as step b) the reaction of the organoborane adduct, generated in step a), with a compound of the general formula (IV)

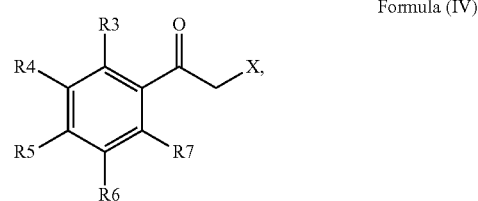

Formula (IV)

where X is a halogen atom and R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms.

In a particularly preferred embodiment of the aforesaid method, X in a compound of the general formula (IV) denotes —Cl or —Br, in particular —Br. In a likewise preferred embodiment of the aforesaid method, a compound of the general formula (IV) in which four of the five aryl substituents R3, R4, R5, R6, and R7 denote hydrogen is preferred. R3, R4, R6, and R7 by preference denote hydrogen, while the substituent in the R5 para-position denotes a halogen atom, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 denotes —Cl, —Br, —$NO_2$, or an alkyl or alkoxy group encompassing 1 to 4 carbon atoms. By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group. The term "hydroboration" is to be understood for purposes of the invention as 1,2-addition of an organoborane reagent to at least one cyclic double bond of the compound of the general formula (III), with the result that a covalent carbon-boron bond, and thus an organoborane adduct, is formed. Suitable methods for hydroboration are described in J. March, Advanced Organic Chemistry, 4th ed., pp. 783-789, to which reference is made here.

The hydroboration is carried out by preference in a solvent. Suitable solvents for hydroboration are, for example, acyclic ethers such as diethyl ether, methyl tert-butyl ether, dimethoxyethane, diethylene glycol dimethyl ether, triethylene glycol dimethyl ether, cyclic ethers such as tetrahydrofuran or dioxan, and hydrocarbons such as hexane or toluene, or mixtures thereof. The reaction temperature is determined as a rule by the reactivity of the hydroboration agent, and is preferably between the melting and boiling points of the reaction mixture. In particular, the reaction can be carried out in THF and/or diethyl ether at temperatures between −100° C. and 40° C., by preference between −40° C. and 30° C., and in particular between 0° C. and 20° C. Suitable organoborane reagents are, by preference, sterically demanding organoborane reagents; these can be selected, for example, from the group consisting of 9-borabicyclo[3.3.1] nonane (9-BBN), 1,1,2-trimethylpropylborane (thexylborane), catecholborane, or diisopinocampheylborane (lpc2BH). The organoborane reagent is preferably used in equimolar fashion or at an excess with reference to the at least one cyclic double bond of the compound of the general formula (III).

An advantage of the aforesaid method is the fact that the organoboron adducts that form preferably do not need to be isolated, but can be reacted directly, without previous purification, with a compound of the general formula (IV). The aforesaid reaction of the organoborane adduct with the compound of the general formula (IV) is accomplished by preference in a suitable solvent, for example in acyclic ethers such as diethyl ether, methyl tert-butyl ether, dimethoxyethane, diethylene glycol dimethyl ether, triethylene glycol dimethyl ether, in cyclic ethers such as tetrahydrofuran or dioxan, and in hydrocarbons such as hexane or toluene, or in mixtures thereof; the above-described reaction can be carried out in greatly preferred fashion in the presence of an alkali metal alcoholate. The reaction temperature is determined as a rule by the reactivity of the compound of the general formula (IV) and/or by the reactivity of the organoboron adduct, and is preferably between the melting and boiling points of the reaction mixture. In particular, the reaction can be carried out in THF and/or diethyl ether at temperatures between −100° C. and 40° C., by preference between −90° C. and 0° C., and in particular between −78° C. and −40° C.

In a greatly preferred embodiment, the aforesaid alkali metal alcoholate is selected from potassium methanolate, sodium methanolate, potassium ethanolate, sodium ethanolate, potassium propylate, sodium propylate, potassium tert-butanolate, sodium tert-butanolate, potassium 2,6-di-tert-butylphenolate, sodium 2,6-di-tert-butylphenolate, and from any mixtures thereof. The alkali metal alcoholate is by preference used in equimolar fashion or at a slight excess (1.05 to 1.30 eq.) with respect to the organoborane adduct that is formed.

Purification of the ketone of the general formula (I) that is formed is accomplished preferably by crystallization, distillation, and/or column chromatography. An advantage of the above-described manufacturing method is the fact that the ketones of the general formula (I) can as a rule be manufactured, directly and economically, in a single-step convergent synthesis without laborious protecting-group operations. What results is thus a scent storage substance AB that is made up substantially of a photoreceptor (A) and a cyclic compound having a cyclic double bond (B). Irradiation then causes the aforesaid scent storage substance AB to decompose again without difficulty into its individual constituents A and B.

A preferred solid, in particular powdered, washing agent according to the present invention can in particular also contain, alongside the ketone according to the present invention (in accordance with formula (I)), components that are selected, for example, from the following:

anionic surfactants such as, by preference, alkylbenzenesulfonate, alkyl sulfate, e.g. in quantities by preference from 5 to 30 wt %, nonionic surfactants such as, by preference, fatty alcohol polyglycol ethers, alkylpolyglucoside, fatty acid glucamide, e.g. in quantities by preference from 0.5 to 15 wt %, detergency builders such as, for example, zeolite, polycarboxylate, sodium citrate, in quantities from, for example, 0 to 70 wt %, advantageously 5 to 60 wt %, by preference 10 to 55 wt %, in particular 15 to 40 wt %, alkalis such as, for example, sodium carbonate, in quantities e.g. from 0 to 35 wt %, advantageously 1 to 30 wt %, by preference 2 to 25 wt %, in particular 5 to 20 wt %, bleaching agents such as, for example, sodium perborate, sodium percarbonate, in quantities e.g. from 0 to 30 wt %, advantageously 5 to 25 wt %, by preference 10 to 20 wt %, corrosion inhibitors, e.g. sodium silicate, in quantities e.g. from 0 to 10 wt %, advantageously 1 to 6 wt %, by preference 2 to 5 wt %, in particular 3 to 4 wt %, stabilizers, e.g. phosphonates, advantageously 0 to 1 wt %, foam inhibitor, e.g. soap, silicone oils, paraffins, advantageously 0 to 4 wt %, by preference 0.1 to 3 wt %, in particular 0.2 to 1 wt %, enzymes, e.g. proteases, amylases, cellulases, lipases, advantageously 0 to 2 wt %, by preference 0.2 to 1 wt %, in particular 0.3 to 0.8 wt %, anti-gray agent, e.g. carboxymethyl cellulose, advantageously 0 to 1 wt %, discoloration inhibitor, e.g. polyvinylpyrrolidone derivatives, advantageously 0 to 2 wt %, adjusting agent, e.g. sodium sulfate, advantageously 0 to 20 wt %, optical brightener, e.g. stilbene derivative, biphenyl derivative, advantageously 0 to 0.4 wt %, in particular 0.1 to 0.3 wt %, optionally further fragrances, optionally water,
optionally soap,
optionally bleach activators,
optionally cellulose derivatives,
optionally dirt repellents,
"wt %" being based in each case on the total agent.

In another preferred embodiment of the invention, the agent is present in liquid form, by preference in gel form. Preferred liquid agents, such as especially washing or cleaning agents as well as cosmetics, have water contents of, for example, 10 to 95 wt %, by preference 20 to 80 wt %, and in particular 30 to 70 wt %, based on the total agent. In the case of liquid concentrates the water content can also be particularly low, e.g. <30 wt %, by preference <20 wt %, in particular <15 wt %, "wt %" being based in each case on the total agent. The liquid agents can also contain non-aqueous solvents.

A preferred liquid, in particular gel-type, washing agent according to the present invention can in particular also contain, alongside the ketone according to the present invention (in accordance with formula (I)), components that are selected e.g. from the following:

anionic surfactants such as, by preference, alkylbenzenesulfonate, alkyl sulfate, e.g. in quantities by preference from 5 to 40 wt %, nonionic surfactants such as, by preference, fatty alcohol polyglycol ethers, alkylpolyglucoside, fatty acid glucamide, for example in quantities by preference from 0.5 to 25 wt %, detergency builders such as, for example, zeolite, polycarboxylate, sodium citrate, advantageously 0 to 15 wt %, by preference 0.01 to 10 wt %, in particular 0.1 to 5 wt %, foam inhibitor, e.g. soap, silicone oils, paraffins, in quantities e.g. from 0 to 10 wt %, advantageously 0.1 to 4 wt %, by preference 0.2 to 2 wt %, in particular 1 to 3 wt %, enzymes, e.g. proteases, amylases, cellulases, lipases, in quantities e.g. from 0 to 3 wt %, advantageously 0.1 to 2 wt %, by preference 0.2 to 1 wt %, in particular 0.3 to 0.8 wt %, optical brightener, e.g. stilbene derivative, biphenyl derivative, in quantities e.g. from 0 to 1 wt %, advantageously 0.1 to 0.3 wt %, in particular 0.1 to 0.4 wt %, optionally further fragrances, optionally stabilizers, water, optionally soap, in quantities e.g. from 0 to 25 wt %, advantageously 1 to 20 wt %, by preference 2 to 15 wt %, in particular 5 to 10 wt %, optionally solvent (by preference alcohols), advantageously 0 to 25 wt %, by preference 1 to 20 wt %, in particular 2 to 15 wt %, "wt %" being based in each case on the total agent.

A preferred liquid fabric softener according to the present invention can in particular also contain, alongside the ketone according to the present invention (in accordance with formula (I)), components that are selected from the following:

cationic surfactants, such as especially esterquats, e.g. in quantities from 5 to 30 wt %, cosurfactants such as, for example, glycerol monostearate, stearic acid, fatty alcohols, fatty alcohol ethoxylates, e.g. in quantities from 0 to 5 wt %, by preference 0.1 to 4 wt %, emulsifiers such as, for example, fatty amine ethoxylates, e.g. in quantities from 0 to 4 wt %, by preference 0.1 to 3 wt %, optionally further scents, dyes, by preference in the ppm range, stabilizers, by preference in the ppm range, solvents such as, in particular, water, in quantities by preference from 60 to 90 wt %, "wt %" being based in each case on the total agent.

EXAMPLES

Example 1

Preparation of a Ketone of the General Formula (I)

Synthesis of 3-(6,6-dimethylbicyclo[3.1.1]-heptan-2-yl)-1-phenylpropan-1-one

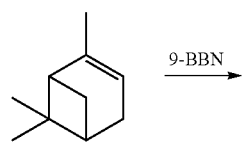

-continued

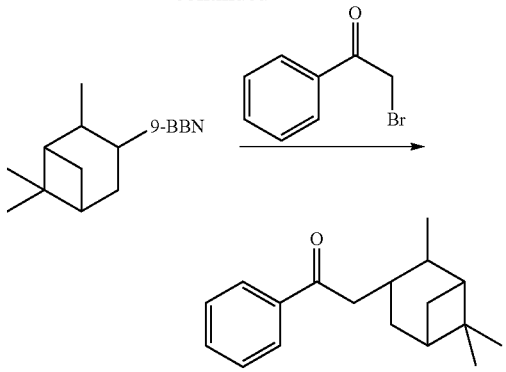

1.36 g (−)-α-pinene (10 mmol) was dissolved in 5 ml THF. To this solution, 21 ml of a 0.5-molar solution of 9-BBN (9-borabicyclo[3.3.1]nonane) in THF (10.5 mmol) was added at 0° C. The reaction mixture was slowly brought to room temperature, and stirred for a further 3 hours. The resulting solution was cooled to −78° C., and a solution of 1.12 g potassium tert-butanolate (10 mmol) in 10 ml THF was then added to the cooled reaction solution. After a short time, 2 g α-bromacetophenone (10 mmol) was added in portions, with constant stirring. The reaction mixture was slowly brought to room temperature, and stirred for 4 hours at room temperature. The resulting product mixture had 50 ml n-pentane added to it, and was washed three times in each case with 10 ml of a 3N sodium hydroxide solution and with 10 ml water. The organic phase was dried over magnesium sulfate. Solvent was removed from the filtrate at reduced pressure. The raw product was purified by column chromatography. 140 mg (10%) of the aforesaid product was obtained.

Example 2

Exposing the Reaction Product from Example 1 to Light 20 mg of the reaction product from Example 1 was dissolved in 8 ml methanol. The reaction solution was exposed in a multiple-lamp photoreactor (8 W lamps×4, Luxchem) with an emission maximum □=350 nm for one hour. The reaction was tracked using GC/MS spectrometry. After at most 60 minutes of exposure, the largely complete conversion of the aforesaid reaction product into acetophenone and α-pinene was observed.

Example 3

Odor Test

For the odor test described below, 0.2 mmol of the reaction product from Example 1 was dissolved in 1 ml acetone. An odor strip was immersed to a depth of 2 cm in the solution, and then dried in the absence of light at 20° C.

For comparison, solutions of 0.1 mmol alpha-pinene and 0.1 mmol acetophenone each in 1 ml acetone, and a mixture of 0.1 mmol alpha-pinene and 0.1 mmol acetophenone in 1 ml acetone, were prepared. An odor strip was then immersed to a depth of 2 cm in each solution, and each odor strip was then dried at 20° C. in the absence of light.

After successful drying, each odor strip was irradiated over the entire testing time period with a commercial fluorescent tube (neutral white [NW] per DIN 5035; color temperature 3300 to 5500 K), and the scent intensity was determined at the respective times indicated.

The scent intensity was evaluated by three trained testers on a scale from 0 to 6, 6 being the highest score and 0 denoting no scent perceived.

Definition of scoring scale:

| | |
|---|---|
| 6 | unpleasantly strong |
| 5 | very strong |
| 4 | strong |
| 3 | intense |
| 2 | pleasant |
| 1 | perceptible |
| 0 | no longer perceptible |

The results of the odor test are presented in the table below; the values indicated reflect the range of odor perception of the tester group.

| | after 1 minute | after 20 minutes | after 45 minutes | after 1.5 hours | after 24 hours |
|---|---|---|---|---|---|
| Photocaged pinene | strong chemical smell of acetophenone 1 | 0-1 | 0-1 | 0 can be smelled again with use of daylight lamp 1 | 0 can be smelled again with use of daylight lamp 1 |
| Acetophenone | 3 | 3 | 2-3 | 2 | 0 |
| Alpha-pinene | 0-1 | 0 | 0 | 0 | 0 |
| Acetophenone/ alphapinene | only acetophenone perceptible 2-3 | 2-3 | 2 | 2 | 0 |

It is evident that approximately 1 minute of irradiation with a 20 watt daylight lamp (LifeLite Full Spectrum Daylight Lamp) produces, even after 24 hours, photoinduced release of the alpha-pinene odor compound.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A washing or cleaning agent comprising at least one ketone of the general formula (I) in quantities of between 0.0001 and 5 wt. %, based on the total agent:

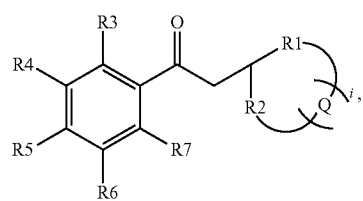

Formula (I)

where i=1 or 2,
R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms, and
R1 and R2, mutually independently, denote a secondary, tertiary, or quaternary carbon atom, and
Q denotes at least one divalent substituted or unsubstituted group bridging R1 and R2 and having 1 to 10 carbon atoms.

2. The washing or cleaning agent according to claim 1, wherein i=2 and Q comprises at least one bridging group encompassing 2 to 6 carbon atoms.

3. The washing or cleaning agent according to claim 1, wherein one or more of R1, R2, and at least one divalent group Q bridging R1 and R2 comprises a substitution with at least one heteroatom selected from the group consisting of N, O, or S.

4. The washing or cleaning agent according to claim 1, wherein four of the five aryl substituents R3, R4, R5, R6, and R7 denote hydrogen.

5. The washing or cleaning agent according to claim 1, wherein by cleavage of a carbon bond, a ketone of the general formula (II)

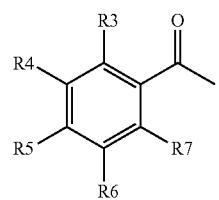

Formula (II)

and a compound of the general formula (III)

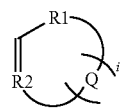

Formula (III)

are formable.

6. The washing or cleaning agent according to claim 5, wherein the compound of the general formula (III) in claim 5 is a cyclic terpene or cyclic terpenoid having at least one cyclic double bond.

7. The washing or cleaning agent according to claim 6, wherein the cyclic terpene or cyclic terpenoid is selected from the group consisting of α-pinene, α-terpinene, limonene, β-bisabolene, humulene, terpinolene, phellandrene, trichodiene, and from enantiomers and/or diastereomers thereof.

8. A method for long-lasting scenting of surfaces, comprising:
applying the washing or cleaning agent according to claim 1 onto the surface to be scented, and
exposing said surface to an electromagnetic radiation encompassing the wavelengths from 200 to 400 nm.

9. The method according to claim 8, wherein the step of applying the washing or cleaning agent onto the surface to be scented comprises applying a washing or cleaning agent comprising the ketone onto the surface to be scented.

10. A method for manufacturing the ketone of the general formula (I) in accordance with claim 1, comprising:
a) hydroborating a compound of the general formula (III)

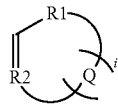

Formula (III)

where i=1 or 2, and R1 and R2, mutually independently, denote a secondary, tertiary, or quaternary carbon atom and Q denotes at least one divalent substituted or unsubstituted group bridging R1 and R2 and having 1 to 10 carbon atoms, b) reacting the organoborane adduct produced in step a) with a compound of the general formula (IV)

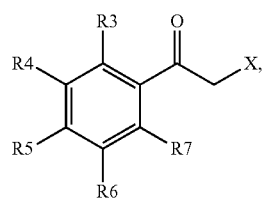

Formula (IV)

where X is a halogen atom and R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms.

* * * * *